US006390986B1

(12) United States Patent
Curcie et al.

(10) Patent No.: US 6,390,986 B1
(45) Date of Patent: May 21, 2002

(54) CLASSIFICATION OF HEART RATE VARIABILITY PATTERNS IN DIABETICS USING CEPSTRAL ANALYSIS

(75) Inventors: David J. Curcie, Toms River; William Craelius, Somerset, both of NJ (US)

(73) Assignee: Rutgers, The State University of New Jersey, Piscataway, NJ (US)

( * ) Notice: Subject to any disclaimer, the term of this patent is extended or adjusted under 35 U.S.C. 154(b) by 0 days.

(21) Appl. No.: 09/494,572

(22) Filed: Jan. 31, 2000

Related U.S. Application Data

(60) Provisional application No. 60/136,651, filed on May 27, 1999.

(51) Int. Cl.$^7$ .................................................. A61B 5/00
(52) U.S. Cl. ........................ 600/485; 600/500; 600/300
(58) Field of Search ................................ 600/500, 485, 600/300

(56) References Cited

U.S. PATENT DOCUMENTS 5,976,081 A * 11/1999 Silverman ................... 600/300

OTHER PUBLICATIONS

Mukhopadhyay, et al., "Parametric Modeling of ECG Signal," Med. Biol. Eng. Comput., 4:171–173 (1996).
Murthy, et al., "Homomorphic Analysis and Modeling of ECG Signals," IEEE Trans. Biomed. Eng., BME–26(5):330–344 (1979).
Pagani, et al., "Spectral Analysis of Heart Rate Variability in the Assessment of Autonomic Diabetic Neuropathy," Journal of the Autonomic Nervous System, vol. 23, No. 2, pp. 143–153 (1998).

Raymond, et al., "Classification of Heart Rate Variability in Patients with Mild Hypertension," Australasian Physical and Engineering Sciences in Medicine, vol. 20, No. 4, pp. 207–213 (1997).
Raymond, et al., "Visualization of Heart Rate Variability Data Using Topographic Mappings," Computers in Cardiology (1998).
Silipo, et al., "Neutral and Traditional Techniques in Diagnostic ECG Classification," ICASSP, IEEE International Conference on Acoustics, Speech and Signal Processing—Proceedings, 1:123–126 (1997).
Weise, et al., "Age Related Changes in Heart Rate Power Spectra in Diabetic Man During Orthostasis," Diabetes Research and Clinical Practice, vol. 11, pp. 23–32 (1991).
Bellavere, et al., "Power Spectral Analysis of Heart–Rate Variations Improves Assessment of Diabetic Autonomic Neuropathy," Diabetes, vol. 41, pp. 633–640 (1991).
Curcie, et al., "Heart Rate Complexity as a Diagnostic of Autonomic Neuropathy from Insulin Dependent Diabetes Mellitus," PACE, Apr. (1998).
Curcie, et al., "Recognition of Individual Heart Rate Patterns with Cepstral Vectors," Biological Cybernetics, vol. 77, pp. 103–109 (1997).
Freeman, et al., "Spectral Analysis of Heart Rate in Diabetic Autonomic Neuropathy," Archives of Neurology, vol. 48, pp. 185–190 (1991).

* cited by examiner

Primary Examiner—Robert L. Nasser
(74) Attorney, Agent, or Firm—Wolff & Samson

(57) ABSTRACT

An encoding and classification method is provided which is capable of comprehensively featuring relevant spectral information for the early detection of diabetes-induced cardiac autonomic neuropathy using the LP-cepstral discriminant classifier for quick, noninvasive assessment (screening) of neuropathy in diabetics. Patients are tested in the supine position thus avoiding the stresses to the patient that are associated with tilt table testing.

22 Claims, 5 Drawing Sheets

FIG. 2A

| (a) SUPINE | | | | | | |
|---|---|---|---|---|---|---|
| SUBJECT | MEAN | STd.D | VLF | LF | HF | TP | LF/HF |
| D1 | 76.1 | 2.1 | 3.27 | 0.86 | 0.5 | 4.6 | 1.7 |
| D2 | 56.7 | 2.06 | 1.71 | 1.31 | 1.24 | 4.26 | 1.05 |
| D3 | 76.7 | 2.8 | 6.55 | 3.2 | 0.6 | 10.3 | 5.36 |
| D4 | 77.3 | 3.7 | 6.85 | 5.5 | 3.5 | 16 | 1.56 |
| D5 | 66.5 | 1.5 | 2.01 | 0.48 | 0.11 | 2.61 | 4.4 |
| D6 | 81.4 | 2.35 | 2.2 | 2.89 | 0.7 | 5.7 | 4.21 |
| D7 | 79.6 | 1.82 | 1.42 | 0.53 | 0.4 | 2.35 | 1.3 |
| D8 | 78.7 | 1.8 | 0.84 | 0.64 | 1.25 | 2.7 | 0.52 |
| D9 | 68.6 | 5.53 | 20.6 | 6.5 | 1.7 | 28.8 | 3.9 |
| D10 | 73.6 | 3.4 | 6.9 | 3 | 1.2 | 11.1 | 2.4 |
| D12 | 87.2 | 2.16 | 2.6 | 1.5 | 0.5 | 4.6 | 3.14 |
| D15 | 69.4 | 3.7 | 7.6 | 4.3 | 2.4 | 14.4 | 1.78 |
| D21 | 48.7 | 1.26 | 0.88 | 0.42 | 0.31 | 1.6 | 1.38 |
| D11 | 79.5 | 1.71 | 1.28 | 0.93 | 0.53 | 2.75 | 1.74 |
| D13 | 76.6 | 4.5 | 16.06 | 7.8 | 1.15 | 25 | 6.71 |
| D14 | 71.4 | 2.03 | 1.7 | 1.46 | 0.2 | 3.3 | 7.18 |
| D16 | 73.2 | 2.1 | 3.31 | 0.91 | 0.11 | 4.3 | 8 |
| D17 | 61.4 | 2.5 | 1.6 | 1.31 | 0.95 | 3.8 | 1.37 |
| D18 | 72.2 | 4 | 12.1 | 8.4 | 1.4 | 22 | 5.8 |
| D19 | 63.8 | 1.5 | 1.84 | 0.27 | 0.08 | 2.2 | 3.45 |
| D20 | 71.8 | 1.51 | 1.8 | 0.38 | 0.13 | 2.35 | 2.8 |

FIG. 2B

| (c) | | |
|---|---|---|
| ΔHR | S/P | T/S |
| 0.10 | 3.60 | 2.29 |
| 17.70 | 4.27 | 3.14 |
| 17.20 | 5.00 | 1.40 |
| 11.80 | 6.31 | 2.37 |
| 2.70 | 2.73 | 1.50 |
| 5.60 | 11.57 | 3.18 |
| -3.70 | 2.43 | 1.69 |
| 0.80 | 0.25 | 1.31 |
| 19.00 | 7.76 | 2.21 |
| 7.20 | 1.33 | 1.92 |
| 5.10 | 1.24 | 1.49 |
| 20.00 | 0.58 | 3.03 |
| 6.90 | 14.52 | 3.99 |
| 0.90 | 2.94 | 1.00 |
| 6.40 | 1.37 | 0.19 |
| 16.60 | 5.15 | 0.58 |
| 7.10 | 3.00 | 0.85 |
| 0.50 | 0.22 | 0.13 |
| 4.80 | 1.14 | 0.95 |
| 2.80 | 4.00 | 0.30 |
| 5.70 | 1.54 | 0.55 |

FIG. 2C

| (b) TILT | | | | | | | |
|---|---|---|---|---|---|---|---|
| SUBJECT | MEAN | ST.D | VLF | LF | HF | TP | LF/HF |
| D1 | 76.2 | 2.3 | 2.5 | 1.8 | 0.45 | 4.8 | 3.9 |
| D2 | 74.4 | 3.9 | 7.75 | 5.3 | 1.6 | 14.6 | 3.3 |
| D3 | 93.9 | 2.8 | 3.7 | 3 | 0.4 | 7.1 | 7.5 |
| D4 | 89.1 | 6.54 | 11.75 | 22.1 | 6 | 40 | 3.7 |
| D5 | 69.2 | 1.7 | 2.7 | 0.3 | 0.04 | 3.1 | 6.6 |
| D6 | 87 | 3.6 | 3.1 | 8.1 | 0.6 | 11.8 | 13.4 |
| D7 | 75.9 | 1.9 | 3.3 | 0.97 | 0.44 | 4.7 | 2.2 |
| D8 | 79.5 | 1.9 | 1.93 | 0.31 | 0.45 | 2.7 | 0.68 |
| D9 | 87.6 | 5.2 | 14.4 | 13.2 | 1.5 | 29.2 | 8.6 |
| D10 | 80.8 | 2.6 | 3.7 | 1.6 | 0.34 | 5.6 | 4.6 |
| D12 | 92.3 | 2.23 | 3.4 | 0.62 | 0.13 | 4.2 | 4.67 |
| D15 | 89.4 | 4.06 | 19.6 | 1.4 | 0.27 | 21.3 | 5.4 |
| D21 | 55.6 | 2.9 | 4.5 | 4.5 | 0.8 | 9.8 | 5.5 |
| D11 | 80.4 | 2.45 | 3.01 | 1.56 | 0.9 | 5.47 | 1.75 |
| D13 | 83 | 2.15 | 3.6 | 1.57 | 1.23 | 6.4 | 1.27 |
| D14 | 88 | 2.45 | 3.06 | 1.03 | 0.24 | 4.3 | 4.19 |
| D16 | 80.3 | 2.02 | 3.2 | 0.33 | 0.05 | 3.6 | 6.8 |
| D17 | 61.9 | 2.05 | 2.41 | 0.21 | 1.2 | 3.8 | 0.18 |
| D18 | 77 | 2.4 | 3 | 1.6 | 0.3 | 4.9 | 5.5 |
| D19 | 66.6 | 1.56 | 1.7 | 0.32 | 0.3 | 2.3 | 1.04 |
| D20 | 77.5 | 1.16 | 0.91 | 0.2 | 0.13 | 1.25 | 1.54 |

FIG. 2D

| (d) CORRELATION | |
|---|---|
| $\Delta$ HR vs S/P: | c=.26 |
| HR vs T/S: | c=.33 |
| S/P vs T/S: | c=.63^ |

|  |  | HEART RATE (BPM) | LF/HF | S/P |
|---|---|---|---|---|
| CONTROLS^ | SUPINE | 81±15 | 4.0±2.0^ | 3.0±2.0 |
|  | TILT | 89±13 | 13±7.0^ |  |
| DIABETICS | SUPINE | 71±8.9 | 3.3±2.2 | 3.9±3.7 |
|  | TILT | 79±9.9 | 4.4±3.1 |  |

| STEP | HRCV COEFFICIENT | | F | SIGNIF. (p) | CORRELATION WITH (LF/HF) SUPINE |
|---|---|---|---|---|---|
|  | ENTERED | NOT ENTERED |  |  |  |
| 1 | 11 |  | 8.9 | .008 | -0.88 |
| 2 | 3 |  | 7.7 | .004 | -0.02 |
| 3 | 12 |  | 5.3 | .009 | -0.87 |
| 4 | 4 |  | 4.4 | .014 | -0.43 |
| 5 | 8 |  | 3.4 | .029 | -0.79 |
| 6 | 9 |  | 3.1 | .037 | -0.78 |
| 7 | 6 |  | 2.9 | .048 | -0.59 |
| 8 | 1 |  | 2.8 | .051 | -0.56 |
| 9 | 2 |  | 2.6 | .067 | -0.47 |
| 10 | 7 |  | 2.2 | .111 | -0.64 |
| - |  | 5 | 1.9 | - | -0.53 |
| - |  | 10 | 1.8 | - | -0.80 |

FIG. 5

| HRCV COEFFICIENT | LDF COEFFICIENTS |
|---|---|
| 1 | -3.308 |
| 2 | 1.819 |
| 3 | 1.402 |
| 4 | 0.854 |
| 5 | ---- |
| 6 | 2.525 |
| 7 | -0.830 |
| 8 | -1.480 |
| 9 | 1.451 |
| 10 | ---- |
| 11 | -2.771 |
| 12 | 1.799 |

|  |  |  | PREDICTED GROUP MEMBERSHIP | | TOTAL |
|---|---|---|---|---|---|
|  |  |  | ND | AN |  |
| ORIGINAL | COUNT | ND | 11 | 2 | 13 |
|  |  | AN | 1 | 7 | 8 |
|  | PERCENT | ND | 84.6 | 15.4 | 100 |
|  |  | AN | 12.5 | 87.5 | 100 |

CLASSIFICATION OF HEART RATE VARIABILITY PATTERNS IN DIABETICS USING CEPSTRAL ANALYSIS

RELATED APPLICATIONS

This application claims the benefit of the filing date of U.S. Provisional Application Serial No. 60/136,651, filed May 27, 1999.

BACKGROUND OF THE INVENTION

1. Field of the Invention

The present invention generally relates to a method for screening individuals for autonomic neuropathy (AN), a complication of diabetes mellitus, using cepstral encoding of heart rate (HR) signals. More specifically, the present invention relates to a method for screening individuals for AN using linear predictor-derived cepstral encoding of HR signals obtained from individuals in a supine position.

2. Related Art

Once diabetic AN becomes clinically evident, the estimated 5-year mortality is approximately 50%. Thus, the early detection of autonomic dysfunction is important for effective therapeutic intervention. Thorough diagnosis and evaluation requires a patient history and neurologic examination, that can include nerve conduction studies, needle EMG measurements, vibratory perception thresholds, and a widely accepted battery of cardiovascular function tests evaluated as the Ewing score. Specialized electronic devices also offer a means for clinical assessment. Other indicators are typically used for standard clinical assessment, including impaired vision (retinopathy), and numbness or tingling of the extremities (impaired circulation). However, it would be desirable to employ an accurate, non-invasive method for detecting AN in diabetics. Works of others in this and related areas include the following:

Patterns found in the surface electrocardiogram (ECG) have been studied extensively for the purpose of classifying abnormal waveform profiles. Automated ECG classification has been successfully implemented in clinical practice with useful results for screening, diagnosis, and monitoring. Abenstein, "Algorithms for Real Time Ambulatory ECG Monitoring," Biomed Sci Instrum., 14:73–79 (1978). Representation of the ECG pattern has included Fourier analysis, complex cepstrum, and the autoregressive (AR/ARMA) model. Murthy, et al., "Homomorphic Analysis and Modeling of ECG Signals," IEEE Trans. Biomed Eng., BME-26(5):330–344 (1979), Mukhopadhyay, et al., "Parametric modeling of ECG Signal," Med. Biol. Eng. Comput., 4:171–173(1996). Classification approaches have included frequency analysis, template matching cluster analysis, and most recently, neural networks. Silipo, et al., "Neural and Traditional Techniques in Diagnostic ECG Classification, ICASSP, IEEE International Conference on Acoustics, Speech and Signal Processing—Proceedings, 1:123–126 (1997).

Curcie, et al., "Recognition of Individual Heart Rate Patterns with Cepstral Vectors," Biological Cybernetics, Vol. 77, pages 103–109 (1997), shows that LP-derived cepstral coefficients can be used in a weighted nearest-mean classifier to successfully discriminate HRV (heart rate variability) tachograms for individuals, and that cepstral distance can be used to discriminate between normal and cardiac patient groups.

Bannister, "Autonomic Failure: A Textbook of Clinical Disorders of the Autonomic Nervous System", (1988), Oxford/New York, Oxford University Press, reported that, as a complication of diabetes mellitus, AN is characterized by widespread degeneration of the small nerve fibers of both the sympathetic and parasympathetic tracts.

Stys, et al., "Current Clinical Applications of Heart Rate Variability", Clinical Cardiology, Vol. 21, No. 10, pages 719–724, (1998), noted that spectral analysis of heart rate variability is widely considered to be a reliable noninvasive test for quantitative clinical assessment of cardiac-autonomic regulation.

The onset of cardiac AN, such as that encountered by long term diabetics, has been shown to reflect reductions in energies in both the LF (low frequency) and HF (high frequency) spectral bands, and total power compared to controls, Freeman, et al., "Spectral Analysis of Heart Rate in Diabetic Autonomic Neuropathy", Archives of Neurology Vol. 48, Pages 185–190 (1991); Weise et al., "Age Related Changes in Heart Rate Power Spectra in Diabetic Man During Orthostasis", Diabetes Research and Clinical Practice, Vol. 11, pages 23–32 (1991); Bellavere, et al., "Power Spectral Analysis of Heart-Rate Variations Improves Assessment of Diabetic Autonomic Neuropathy," Diabetes, Vol. 41, pages 633–640 (1991); and Howorka,et al., "Optimal Parameters of Short-Term Heart Rate Spectrogram for Routine Evaluation of Diabetic Cardiovascular Autonomic Neuropathy," Journal of Autonomic Nervous System, Vol. 69, No. 2–3, pages 164–172 (1998).

The reduced change in autonomic balance during orthostatic load, measured via spectral band indices, is a clinical indicator of AN and dysautonomia. In studies, the increase in LF and LF/HF and the decrease in HF produced by tilt were found to be significantly lower in diabetics, than in controls, Pagani, et al., "Spectral Analysis of Heart Rate Variability in the Assessment of Autonomic Diabetic Neuropathy," Journal of the Autonomic Nervous System, Vol. 23, No. 2, pages 143–153 (1998); Lagi, et al., "Power Spectrum Analysis of Heart Rate Variations in the Early Detection of Diabetic Autonomic Neuropathy, Clinical Autonomic Research, Vol. 4, No. 5, pages 245–248 (1994). Abnormal autonomic response to tilt in diabetics with a higher severity of cardiac AN has been shown to include a decrease in LF/HF ratio, Pagani, et al.

Signal classification techniques based on HRV indices have recently been applied to investigating HRV. Raymond et al., "Classification of Heart Rate Variability in Patients with Mild Hypertension," Australasian Physical and Engineering Sciences in Medicine, Vol. 20, No. 4, pages 207–213 (1997), used spectral and time domain indices during rest and isometric handgrip as features in a Bayesian classifier to detect hypertension. Raymond et al. "Visualization of Heart Rate Variability Data Using Topographic Mappings, Computers in Cardiology," (1998), further used topographic mapping of HRV log spectral distance measures to demonstrate a clustering effect corresponding to both tilt, and the presence or absence of beta blockade in healthy subjects.

Prognostic classifiers offer a potentially powerful clinical tool for identifying the onset of cardiac neuropathy. Curcie et al., Heart Rate Complexity as a Diagnostic of Autonomic Neuropathy from Insulin Dependent Diabetes Mellitus," PACE, April, (1998) showed that fractal dimension, a non-linear measure of signal complexity, could be used on supine HR records to predict the outcome of tilt in diabetics, a possible indicator of AN, as measured by the change in the LF/HF index.

The onset of cardiac autonomic neuropathy progresses independently from somatic neuropathy, and though no connection was found between power spectrum analysis and somatic neuropathy, spectral indices are sensitive enough to detect cardiac autonomic neuropathy in diabetics where standard methods sometimes fail. Thus, an encoding and classification method capable of comprehensively featuring relevant spectral information would be useful for the early detection of diabetes-induced cardiac AN.

None of the work by others has resulted in a method for screening diabetics for AN using cepstral vector analysis of heart rate signals. The method of the present invention demonstrates that the LP-cepstral discriminant classifier is useful and reliable for quick, noninvasive assessment (screening) of neuropathy in diabetics, while avoiding the stresses to the patient that are associated with tilt table testing.

OBJECTS AND SUMMARY OF THE INVENTION

A principal object of the present invention is the provision of a method for detecting AN in patients.

Another object and advantage of the present invention is the provision of a method for detecting AN in patients using heart rate variability indications from the patient and from a control group.

Even another object and advantage of the present invention is the provision of a method for detecting AN which encodes the heart rate signals with linear-predictive cepstral encoding to create heart rate cepstral vectors (HRCV).

Still another object and advantage of the present invention is the provision of a method in which cepstral encoding of HRV provides a new identifier of the possible early onset of cardiac autonomic neuropathy.

Still a further object and advantage of the present invention is the provision of an encoding and classification method capable of comprehensively featuring relevant spectral information for the early detection of diabetes-induced cardiac AN.

An additional object and advantage of the present invention is the use of the LP-cepstral discriminant classifier for quick, noninvasive assessment (screening) of neuropathy in diabetics, while avoiding the stresses to the patient that are associated with tilt table testing.

Even an additional object and advantage of the present invention is the provision of a diabetic neuropathy screening method which is useful and reliable.

Still even an additional object and advantage of the present invention is the use LP-cepstral encoding and pattern classification as a clinical test of autonomic function in patients with known or suspected cardiac autonomic dysfunction.

Yet even an additional object and advantage of the present invention is the use of a discriminant classifier based on supine HR cepstral vectors from a population of diabetics.

The present invention relates to a method for screening individuals for AN using cepstral encoding of HR signals. Preferably, linear predictor-derived cepstral encoding of the heart rate signals are obtained from individuals in a supine position to generate a vector. The vector is compared with a classifier heart rate cepstral vector generator from a population having AN. The heart rate cepstral vector is compared with the classifier to indicate presence or absence of AN in the individual. The invention removes the need for utilizing a tilt table to diagnose AN. Approximately fifteen minutes of heart rate data from an individual in a supine position is sufficient for diagnosis.

BRIEF DESCRIPTION OF THE DRAWINGS

Other important objects and features of the invention will be apparent from the following Detailed Description of the Invention taken in connection with the accompanying drawings in which:

FIGS. 2(a)–2(d) are tables showing the time domain and spectral analysis results for a diabetic group (a) supine date, (b) tilt data, (c) ΔHR, S/P=$(LF_{tilt}/HF_{supine})$, $$T/S = \frac{(LF/HF)_{tilt}}{(LF/HF)_{supine}}$$

(d) correlation of variables from (c). Subjects with abnormal response to tilt (T/S≦1) are highlighted in gray.

FIG. 3 is a table showing a summary of spectral responses to tilt. Mean LF/HF was significantly greater for controls FIG. 4 is a table showing stepwise discriminant analysis-variables entered/removed, and correlation with the supine LF/HF index. Stepwise analysis terminated at 10 steps because F values of the remaining coefficients, 5 and 10, were insufficient to warrant their entry.

FIG. 5 is a table showing linear discriminant function coefficients for classification of diabetics. These standardized coefficients define a hyperplane separating diabetics specified a priori as with, and without autonomic neuropathy. Coefficients 5 and 10 were not entered into the discriminant analysis.

Figures 6, 7:
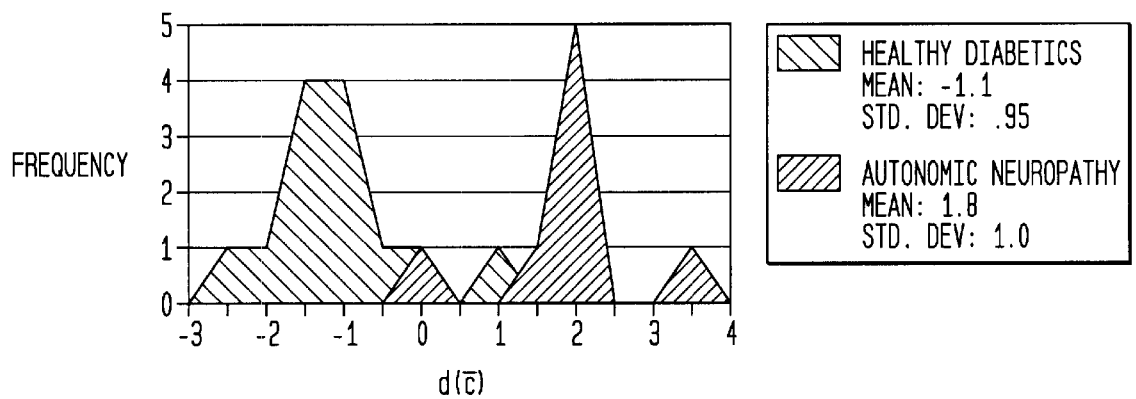

FIG. 6 is a graph showing linear discriminant function results from group discrimination. The decision boundary falls between the two group means, or approximately d $\vec{(c)}$=0.3

FIG. 7 is a table showing discriminant analysis classification results: 85.7% of cross-validated (using the leave-one-out method) grouped cases were correctly classified.

DETAILED DESCRIPTION OF THE INVENTION

The present invention employs of LP-cepstral encoding and pattern classification as a clinical test of autonomic function in patients with known or suspected cardiac autonomic dysfunction. A linear discriminant classifier based on supine HR cepstral vectors from a population of diabetics achieved an accuracy of 87.5% for the positive detection of diabetic cardiac AN. LP-cepstral codebook vectors derived from 15-minute HR epochs are thus adequate to represent HRV indicators, spectral and/or time domain, which reflect the onset of cardiac AN in diabetics. Cepstral encoding of HRV provides a new identifier of the possible early onset of cardiac autonomic neuropathy.

The present invention applies signal classification theory to HRV to screen diabetics for autonomic neuropathy. The theory includes application of formulae and protocols adapted from pattern recognition and speaker recognition research. The classification methods presented consist of: 1) encoding the signal, 2) establishing a template for individual or group classification (referred to as a classifier codebook), 3) calculating custom weights to improve classifier performance, and 4) executing a basic recognition decision criterion. Individual recognition and group classification methods are employed. Group classification is tested on both a Euclidean distance classifier using the nearest-mean criterion, and a discriminant classifier. Class-distance ratios may also be used to demonstrate class separation. Also, cepstral coefficients are correlated with several HRV indices, and cepstral distance measures with respect to the LF and HF spectral indices of autonomic tone are used.

The present invention relates to a method for screening individuals for AN using cepstral encoding of HR signals. Preferably, linear predictor-derived cepstral encoding of the heart rate signals are obtained from individuals in a supine position to generate a vector. The vector is compared with a classifier heart rate cepstral vector generator from a population having AN. The heart rate cepstral vector is compared with the classifier to indicate presence or absence of AN in the individual. The invention removes the need for utilizing a tilt table to diagnose AN. Approximately fifteen minutes of heart rate data from an individual in a supine position is sufficient for diagnosis.

In practice, the method of the present invention comprises recording information about an individual's heart rate while the individual is in a supine position. Heart rate cepstral vectors are then generated for the individual. The cepstral data is statistically matched, with the linear discriminant classifier to cepstral data of either of two control groups, comprising known diabetics, one with neuropathy and one without. The control groups are previously analyzed on a tilt table, and were tilted as is known in the art, and spectro band analysis is used to establish the groups. Then, the individuals comprising the control groups are then positioned in a supine position and then cepstral data is collected so that there is information relating to both of the known groups in a supine position. Thus, the data from an unknown individual can be compared against the two control groups to determine whether or not the unknown individual has AN.

The present invention may be understood by reference to the following example and to Curcie, et al., "Recognition of Individual Heart Rate Patterns with Cepstral Vectors" (1997), supra, and by reference to the thesis of David John Curcie, written under the direction of William Craelius, entitled Classification of Heart Rate Variability Patterns Using Cepstral Vectors submitted to the Graduate School—New Brunswick, Rutgers, The State University in May, 1999, the entire disclosures of which are expressly incorporated herein by reference.

Figure 1:
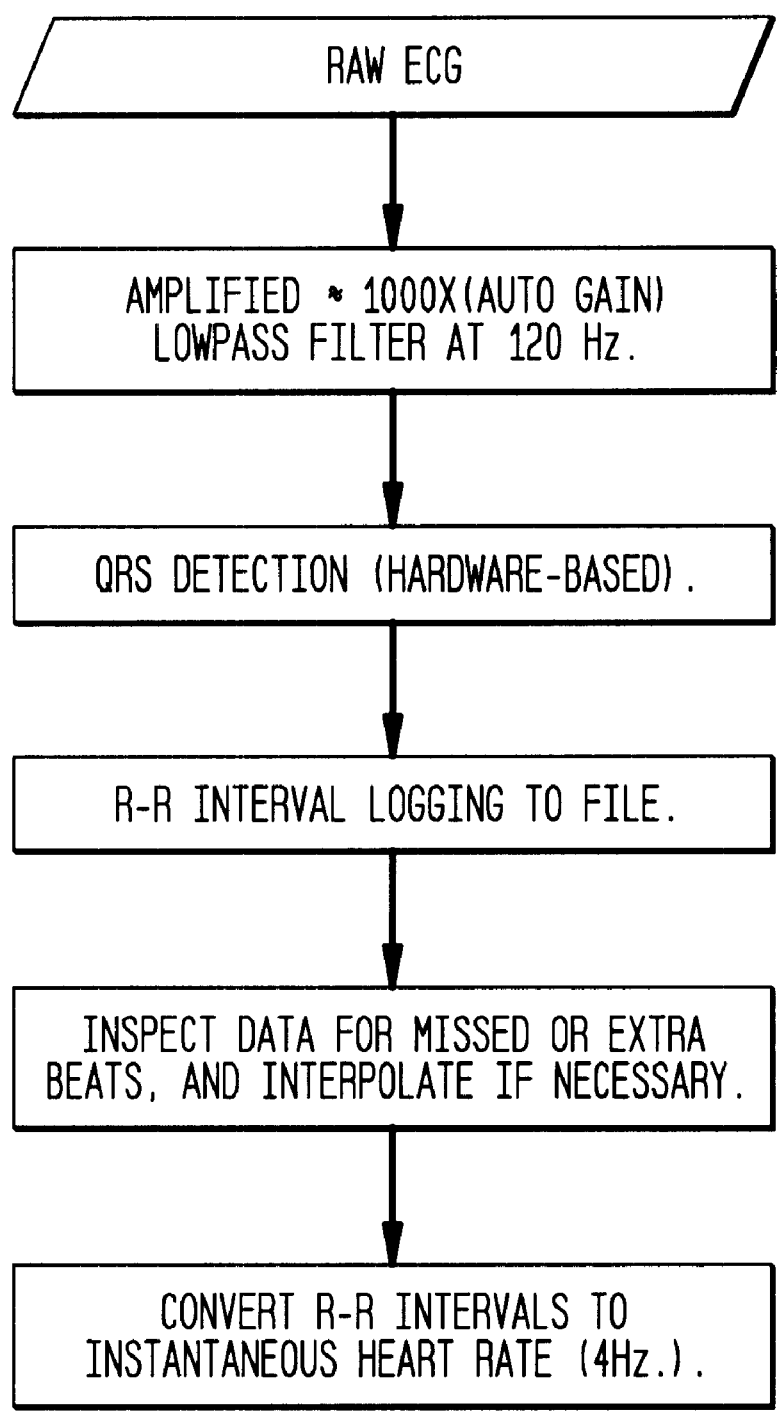
FIG. 1 is a flow chart of cardiac data preprocessing showing the steps for converting raw ECG waveform into a record of instantaneous heart rate.

Twenty-one diabetic patients (10 Male, 11 Female, age 50±14yrs) were recorded under tilt table protocol. The subjects included 8 insulin-dependent and 13 self-regulating (with oral hypoglycemics) diabetics, diagnosed for periods ranging from 1 to 50 years. Subjects were free of drugs other than insulin at the time of recording. Patients were recorded while on an electrically driven tilt table. Subjects were recorded for 15-minute epochs in the supine position, followed by the 70 degrees head-up tilt position. At least 5 minutes were allowed for mean HR stabilization prior to each recording. Inter-beat-intervals were logged using a digital cardiac data logger (one such device being Log-a-Rhythm Ambulatory Heart Rate & Respiration Recorder, disclosed in U.S. Pat. No. 5,333,615, manufactured by Nian-Crae, Inc., Somerset, N.J.), and subsequently examined, preprocessed, and converted to instantaneous heart rate (IHR) using a "c" program based on the method of Berger, et al., "An Efficient Algorithm for Spectral Analysis of Heart Rate Variability,"IEEE Trans. Biomed. Eng., 33(a): 900–904 (1986). FIG. 1 is a flow chart showing the steps of converting raw ECG to IHR.

LP-cepstral encoding of IHR records was done using DADiSP (trademark of DSP Development Corp., Cambridge, Mass.) software program. A custom DADiSP SPL routine is set forth in Appendix A, hereto. HRCVs'were computed in 12 dimensions, from 640-sample (2.7-min.) windows, with 50% overlap. Each 15-minute record produced 10 training vectors. Cardiac autonomic function was assessed by standard heart rate variability measures. Time domain and spectral HRV indices were calculated for each record. Indices included HR mean, variance, spectral energies in the very low frequency (VLF, 0.003–0.04 Hz.), low frequency (LF, 0.04–0.15 Hz.), high frequency (HF, 0.15–0.4 Hz.), and total power (TP, 0.03–0.4 Hz.) bands. Also calculated were the LF/HF ratio, and the ratio of LF in tilt to HF in supine (LFT/HFS), an index of autonomic balance known as the symp-para (S/P) index described by Craelius et al., "Heart Rate Variability as an Index of Autonomic Imbalance in Patients with Recent Myocardial Infraction," Med. Biol. Eng. Comput., Volume 30 (1992), pages 385–388. The ratio of LF/HF in tilt, to LF/HF in supine (T/S) is used as an index of autonomic response to orthostatic stress.

Two diabetic groups were established based on autonomic status, as measured by the T/S index. The groups consisted of diabetics with normal response to tilt (ND), and those with abnormal response to tilt, indicating autonomic neuropathy (AN). Subjects with a T/S>1 were considered ND, and T/S$\leq$1 were considered AN. Standard discriminant analysis was used on the supine HRCVs'to calculate the discriminant function to best separate the ND and AN classes, as defined by the T/S criterion. Stepwise discriminant analysis was done using a statistical software package (SPSS 8.0, SPSS, Inc., Chicago). Error rate was calculated as both the apparent error rate, and the estimated true error rate, using the leave-one-out method.

Concurrent with the discriminant analysis, statistical measures of separation were calculated. The F-ratio provides information about each variable's contribution to the separation of the groups. In the combined stepwise discriminant analysis used here, the F-table was used as a guide for entering or removing new variables to improve classification performance. The canonical correlation was calculated for the discriminant function as the square root of the ratio of the between groups sum of squares, to the total sum of squares. Squared, it is the proportion of the total variability explained by differences between groups.

In a previous tilt-table study involving healthy controls, it was shown that the activity of the sympathetic nervous system relative to the parasympathetic was increased by tilt in all 8 control subjects, as expected, as indicated by their LF/HF ratios Craelius et al., (1992), supra. In contrast, 8 of the 21 diabetic patients in this study experienced a decline in LF/HF upon tilt, indicating autonomic neuropathy (AN). Results from the time domain and spectral analysis are outlined in FIGS. 2(a)–2(d). FIGS. 2(a)–2(c) show the values for all indices, and the separation of ND and AN groups, based on the T/S index. FIG. 2(d) shows correlation between $\Delta$HR and the S/P and T/S indices was weak, at c=0.26 and c=0.33, respectively. The S/P index showed a moderate correlation with T/S, at c=0.63 (p=0.01). Also, unpaired t-tests of supine HR standard deviation, VLF, LF, HF, and TP did not show significant differences between ND and AN subjects grouped via the T/S index (p>0.05), although supine LF/HF was nearly significant at p=0.06.

FIG. 3, a table showing a summary of spectral responses to tilt, shows that movement from supine to tilt produced a significant shift in spectral energy from the high to low frequency bands in the controls, but not in the diabetic group. Average LF/HF for controls increased from 4±2 to 13±7(p<0.01) during tilt, while the diabetic group average LF/HF changed from 3.3±2.2 to 4.4±3.1 following tilt (n.s.). There was no significant difference in the mean S/P indices.

FIGS. 4–6 show the results of the discriminant analysis. At each step, the HRCV coefficient (variable) that maximizes the smallest F-ratio between the groups is entered. During combined stepwise discriminant analysis, no variables met the partial F exclusion criterion during the analysis. Stepwise analysis terminated at 10 steps because F-values of the remaining coefficients, 5 and 10, were insufficient to warrant their entry. The values for the F-statistic given in FIG. 4 suggest that most of the HRCV coefficients contribute to predicting the outcome of tilt. The coefficient with the highest F-value, #11, also had the highest correlation with $(LF/HF)_{supine}$, though the remaining coefficients did not appear to correspond in this manner, suggesting that HRV properties other than (LF/HF) were discriminatory.

The series of standardized discriminant function coefficients that were calculated for the subject population is given in FIG. 5. These values represent the vectoral weights for best discrimination of the diabetic classes defined in this study. The canonical correlation for the analysis was calculated as 0.85. Thus, squaring this value, 72% of the total variability of the cepstral measures is due to interclass differences. FIG. 6 shows the distribution of discriminant values for the ND and AN classes. The decision boundary falls between the two group means, or approximately $\vec{d}(\vec{c})=0.3$. The region of overlap at $\vec{d}(\vec{c})=1$ represents a false positive classification for neuropathy.

As summarized in FIG. 7, cepstral coefficients encoded from supine HR recordings were predictive of AN, since discriminant analysis of codebook vectors from AN diabetics correctly identified 7 of 8 neuropathies, with 2 false positives. Thus, the cepstral classifier had 87.5% sensitivity, an 84.6% specificity, and an overall accuracy of 85.7%.

It should also be noted that the classifier had a slightly higher percentage of false positives (15.4%) over false negatives (12.5%), which is considered a less costly form of misclassification for medical applications.

Having thus described the invention in detail, it is to be understood that the foregoing description is not intended to limit the spirit and scope thereof. What is desired to be protected by Letters Patent is set forth in the appended claims.

What is claimed is:

1. A method of screening for neuropathy in diabetics using cepstral analysis of heart rate comprising the steps of:
   generating electrical signals representing an individual's instantaneous heart rate while the individual is at rest;
   cepstral encoding said electrical signals to generate heart rate cepstral vectors for an individual;
   generating a classifier of heart rate cepstral vectors from a patient population having early diabetic autonomic neuropathy;
   comparing said heart rate cepstral vectors for an individual within said classifier; and
   using the results of said comparison to indicate the presence or absence of autonomic neuropathy in an individual.

2. The method of claim 1 wherein heart rate information is obtained from an individual in a supine position.

3. The method of claim 2 wherein cepstral encoding is linear predictor-derived.

4. The method of claim 3 wherein said heart rate cepstral vectors are presented in 12-dimensions using linear prediction-derived cepstral coefficients.

5. The method of claim 4 wherein instantaneous heart rate and said classifier from a patient population are recorded while patients are in a supine position.

6. The method of claim 5 wherein the AN status of the patient population is known prior to obtaining classifier, and the status is determined by testing the patient population on a tilt table.

7. A method of screening for neuropathy in diabetics using cepstral analysis of heart rate comprising the steps of:
   generating electrical signals indicative of heart rate in patients having diabetic autonomic neuropathy;
   generating electrical signals indicative of heart rate of an individual while the individual is at rest for diagnoses of autonomic neuropathy in the individual;
   encoding said electrical signals to produce heart rate cepstral vectors; and
   comparing said heart rate cepstral vectors for an individual with said heart rate cepstral vectors for patients to determine the presence or absence of autonomic neuropathy in an individual.

8. The method of claim 7 wherein said electrical signals indicative of heart rate are generated with patients and an individual in supine positions.

9. The method of claim 8 wherein patients are first screened for AN on a tilt table.

10. The method of claim 9 wherein the step of establishing said electrical signals indicative of heart rate in persons having autonomic diabetic neuropathy is determined by establishing two diabetic groups based on autonomic status.

11. The method of claim 10 further including the step of using discriminant analysis to calculate a discriminant function to separate the groups.

12. The method of claim 8 wherein said encoding is linear predictor-derived cepstral encoding.

13. The method of claim 8 further including the step of calculating time domain and spectral heart rate variability indices for patients and an individual.

14. The method of claim 13 wherein said indices include heart rate mean, variance, spectral energies in the very low frequency, low frequency, high frequency, and total power bands.

15. The method of claim 14 wherein said very low frequency band is within the range of 0.003–0.04 Hz.

16. The method of claim 14 wherein said low frequency band is within the range of 0.04–15 Hz.

17. The method of claim 14 wherein said high frequency band is within the range of 0.15–0.4 Hz.

18. The method of claim 14 wherein said total power band is within the range of 0.03–0.4 Hz.

19. The method of claim 13 further including the step of calculating low frequency/high frequency ratio.

20. The method of claim 19 further including the step of calculating the ratio of low frequency in tilt to high frequency in supine to generate an index of autonomic balance.

21. A method of screening for neuropathy in diabetics using cepstral analysis of heart rate comprising the steps of:
   sampling a patient's heart rate while the patient is at rest;
   generating electrical signals representing the patient's instantaneous heart rate;
   generating at least one cepstral vector from the electrical signals, said cepstral vector being representative of all power bands of the electrical signals;
   generating a classifier of heart rate cepstral vectors from a patient population having early diabetic autonomic neuropathy;
   comparing the at least one cepstral vector of the patient to one or more cepstral vectors within the classifier; and
   using the results of the comparison to indicate the presence or absence of autonomic neuropathy in the patient.

22. The method of claim 21, wherein the step of generating the classifier comprises applying linear discriminant analysis to the patient population to calculate the classifier.

* * * * *